United States Patent [19]
Yoshitake

[11] Patent Number: 5,945,555
[45] Date of Patent: Aug. 31, 1999

[54] SILATRANE DERIVATIVE, METHOD FOR MANUFACTURING SAME, ADHESION PROMOTER, AND CURABLE SILICONE COMPOSITION

[75] Inventor: Makoto Yoshitake, Chiba Prefecture, Japan

[73] Assignee: Dow Corning Toray Silicone Co., Ltd., Tokyo, Japan

[21] Appl. No.: 09/195,814

[22] Filed: Nov. 19, 1998

[30] Foreign Application Priority Data

Nov. 28, 1997 [JP] Japan .................................. 9-344297

[51] Int. Cl.$^6$ ...................................... C07F 12/10
[52] U.S. Cl. .............................. 556/408; 528/15; 528/31; 528/32; 528/38
[58] Field of Search ............................... 556/408; 528/15, 528/31, 32, 38

[56] References Cited

U.S. PATENT DOCUMENTS

| | | | |
|---|---|---|---|
| 2,953,545 | 9/1960 | Finestone | 260/47 |
| 3,032,576 | 5/1962 | Morehouse | 556/408 |
| 3,133,108 | 5/1964 | Finestone | 556/408 |
| 3,188,921 | 6/1965 | Samour | 556/408 |
| 4,048,206 | 9/1977 | Voronkov et al. | 556/405 |
| 4,072,701 | 2/1978 | Pletka et al. | 556/413 |
| 4,129,585 | 12/1978 | Buder et al. | 556/428 |

FOREIGN PATENT DOCUMENTS 61-069781  2/1986  Japan .

*Primary Examiner*—Paul F. Shaver
*Attorney, Agent, or Firm*—Larry A. Milco

[57] ABSTRACT

A silatrane derivative having the formula:

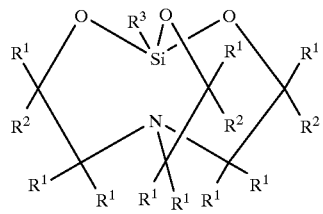

wherein each $R^1$ is independently a hydrogen atom or an alkyl group; each $R^2$ is independently selected from the group consisting of a hydrogen atom, an alkyl group, and an alkenyloxyalkyl group having the general formula:

$$-R^4-O-R^5$$

wherein $R^4$ is an alkylene group and $R^5$ is an alkenyl group, with the proviso that at least one $R^2$ is an alkenyloxyalkyl group; and each $R^3$ is independently selected from the group consisting of a monovalent hydrocarbon group, a $C_1$ to $C_{10}$ alkoxy group, a glycidoxyalkyl group, an oxiranylalkyl group, an acyloxyalkyl group, a haloalkyl group, and an aminoalkyl group.

17 Claims, No Drawings

SILATRANE DERIVATIVE, METHOD FOR MANUFACTURING SAME, ADHESION PROMOTER, AND CURABLE SILICONE COMPOSITION

FIELD OF THE INVENTION

The present invention relates to a silatrane derivative, a method for manufacturing the same, an adhesion promoter comprising the silatrane derivative, and a curable silicone composition containing the adhesion promoter that exhibits specific adhesion to organic resins.

BACKGROUND OF THE INVENTION

A silatrane compound expressed by the general formula:

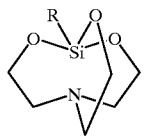

in which R in the above formula is a methyl group, a phenyl group, a methoxy group, or an ethoxy group is a known compound (see U.S. Pat. No. 2,953,545 and Japanese Laid-Open Patent Application 61-69781), but even when these silatrane compounds were added to a curable silicone composition, the product still did not exhibit good adhesion.

SUMMARY OF THE INVENTION

The inventors arrived at the present invention as a result of research into a novel silatrane derivative that would be useful as an adhesion promoter.

Specifically, an object of the present invention is to provide a novel silatrane derivative, an efficient method for manufacturing this silatrane derivative, an adhesion promoter composed of this silatrane derivative, and a curable silicone composition that contains this adhesion promoter and exhibits specific adhesion to organic resins.

The present invention is directed to a silatrane derivative having the formula:

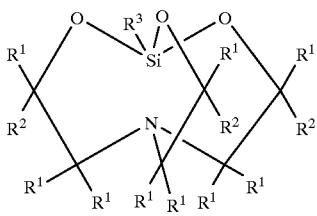

wherein each $R^1$ is independently a hydrogen atom or an alkyl group; each $R^2$ is independently selected from the group consisting of a hydrogen atom, an alkyl group, and an alkenyloxyalkyl group having the formula:

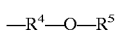

$$-R^4-O-R^5$$

wherein $R^4$ is an alkylene group and $R^5$ is an alkenyl group, with the proviso that at least one $R^2$ is an akenyloxyalkyl group; and each $R^3$ is independently selected from the group consisting of a monovalent hydrocarbon group, a $C_1$ to $C_{10}$ alkoxy group, a glycidoxyalkyl group, an oxiranylalkyl group, an acyloxyalkyl group, a haloalkyl group, and an aminoalkyl group.

The present invention is further directed to a method of preparing the above silatrane derivative, to an adhesion promoter comprising the silatrane derivative, and to a curable silicone composition containing same.

DETAILED DESCRIPTION OF THE INVENTION

The silatrane derivative of the present invention is expressed the general formula:

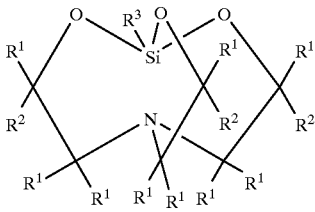

In the above formula, each $R^1$ is independently a hydrogen atom or an alkyl group. Examples of the alkyl group of $R^1$ include methyl, ethyl, propyl, butyl, pentyl, isopropyl, isobutyl, cyclopentyl, and cyclohexyl. It is particularly favorable for $R^1$ to be a hydrogen atom or a methyl group. Each $R^2$ in the above formula is independently selected from the group consisting of a hydrogen atom, an alkyl group, and an alkenyloxyalkyl group expressed by the general formula:

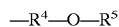

$$-R^4-O-R^5$$

with the proviso that at least one $R^2$ group is an alkenyloxyalkyl group. Examples of the alkyl group of $R^2$ are the same as the alkyl groups listed for $R^1$ above. For the alkenyloxyalkyl group of $R^2$, $R^4$ in the formula is an alkylene group, examples of which include methylene, ethylene, methylmethylene, and propylene, with methylene being preferred. $R^5$ in the above formula is an alkenyl group, examples of which include vinyl, allyl, butenyl, pentenyl, and hexenyl, with a $C_3$ to $C_{10}$ alkenyl group being preferable, and an allyl group being particularly favorable. Examples of the alkenyloxyalkyl group of $R^2$ include an allyloxymethyl group and an allyloxypropyl group. Each $R^3$ in the above formula is independently selected from the group consisting of substituted or unsubstituted monovalent hydrocarbon groups, $C_1$ to $C_{10}$ alkoxy groups, glycidoxyalkyl groups, oxiranylalkyl groups, acyloxyalkyl groups, and aminoalkyl groups. Examples of the monovalent hydrocarbon group of $R^3$ include alkyl groups such as methyl, ethyl, propyl, butyl, pentyl, isopropyl, isobutyl, cyclopentyl, and cyclohexyl; alkenyl groups such as vinyl, allyl, butenyl, and hexenyl; aryl groups such as phenyl, tolyl, and xylyl; arallyl groups such as benzyl and phenethyl; and haloalkyl groups such as chloromethyl, 3-chloropropyl, and 3,3,3-trifluoropropyl; examples of the alkoxy group of $R^3$ include methoxy, ethoxy, and propoxy; examples of the glycidoxyalkyl group of le include 3-glycidoxypropyl; examples of the oxiranylalkyl group or $R^3$ include 4-oxiranylbutyl and an 8-oxiranyloctyl; examples of the acyloxyalkyl group of $R^3$ include acetoxypropyl and a 3-methacryloxypropyl; and examples of the aminoalkyl group of $R^3$ include 3-aminopropyl and N-(2-aminoethyl)-3-aminopropyl.

The following compounds are examples of the silatrane derivative of the present invention:

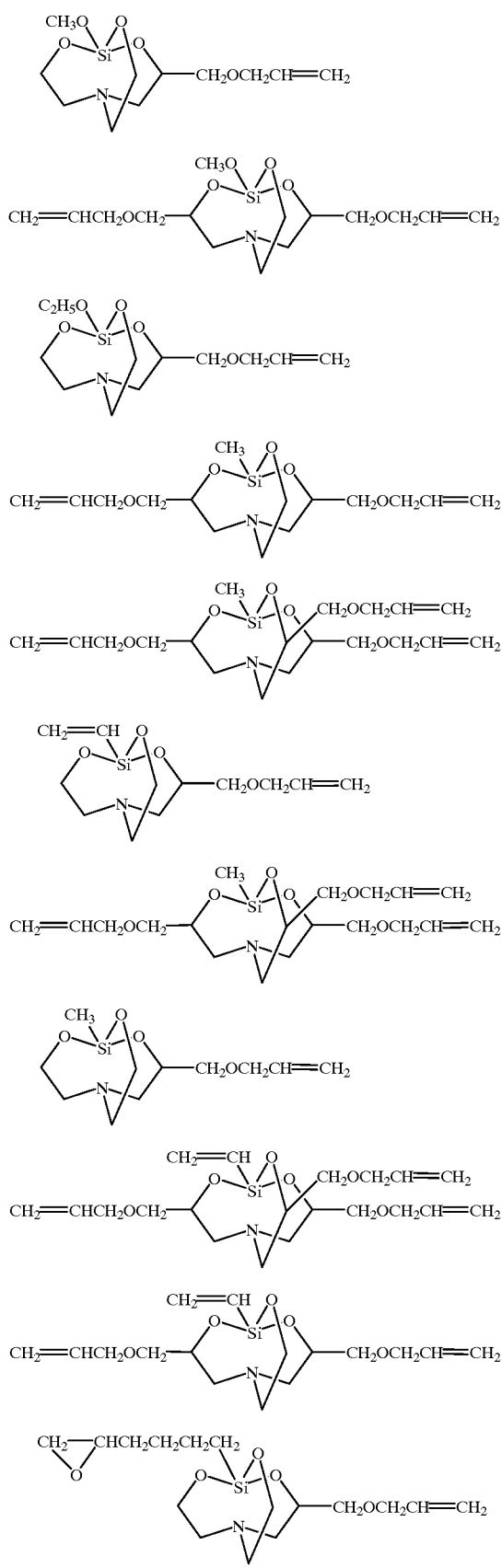

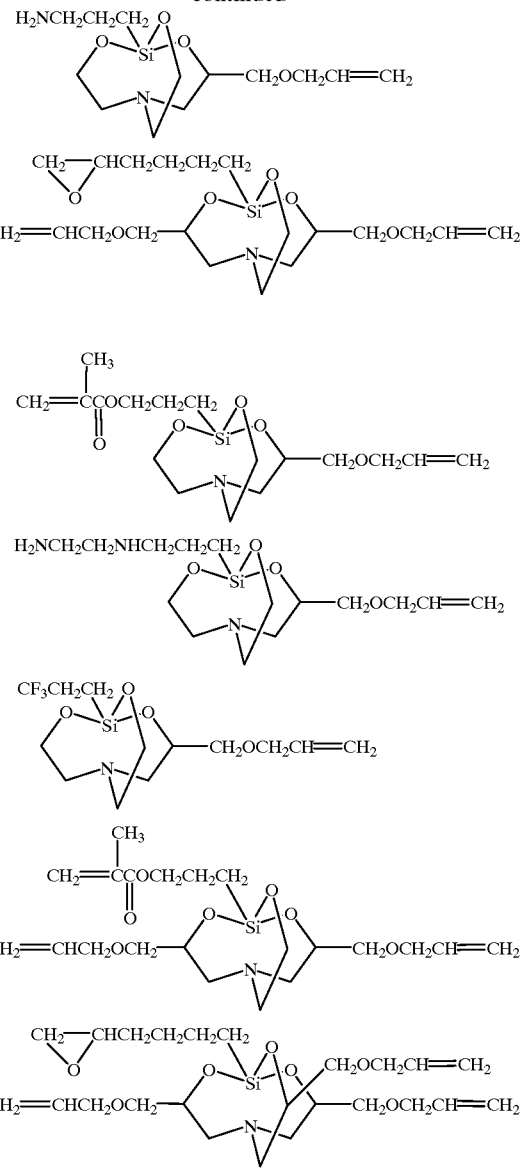

The method of preparing a silatrane derivative according to the present invention comprises reacting an epoxy compound having the formula:

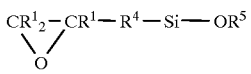

and an alkoxysilane compound having the formula:

with a compound selected from the group consisting of ammonia an an amine compound having the formula:

wherein each $R^1$ is independently a hydrogen atom or an alkyl group; each $R^3$ is independently selected from the group consisting of a monovalent hydrocarbon group, a $C_1$ to $C_{10}$ alkoxy group, a glycidoxyalkyl group, an oxiranylalkyl group, an acyloxyalkyl group, a haloalkyl group, and an aminoalkyl group; $R^4$ is an alkylene group; $R^5$ is an alkenyl group; $R^6$ is a $C_1$ to $C_{10}$ alkyl group; and y is 1 or 2.

The epoxy compound is a raw material for forming the skeleton of the above-mentioned silatrane derivative, and it is also a raw material for introducing alkenyloxyalkyl groups into molecules of the above-mentioned silatrane derivative. In the formula for the epoxy compound, $R^1$, $R^4$, and $R^5$ are as defined above. Preferably $R^5$ is a $C_3$ to $C_{10}$ alkenyl group and more preferably $R^5$ is an allyl group. Examples of this epoxy compound include allyl glycidyl ether and butenyl glycidyl ether.

The alkoxysilane is a raw material for forming the skeleton of the silatrane derivative of the present invention. $R^3$ in the formula for the alkoxysilane is as defined above. $R^6$ in the above formula is a $C_1$ to $C_{10}$ alkyl group, examples of which include methyl, ethyl, and propyl. Examples of this alkoxysilane compound include tetramethoxysilane, tetraethoxysilane, methyltrimethoxysilane, methyltriethoxysilane, vinyltrimethoxysilane, vinyltriethoxysilane, phenyltrimethoxysilane, 3-methacryloxypropyltrimethoxysilane, 3,3,3-trifluoropropyltrimethoxysilane, nonafluorobutylethyltrimethoxysilane, 3-aminopropyltrimethoxysilane, 3-aminopropyltriethoxysilane, and N-(2-aminoethyl)-3-aminopropyltrimethoxysilane.

The ammonia or amine compound is a raw material for forming the skeleton of the silatrane derivative of the present invention. $R^1$ in the formula for the amine compound is as defined above and y is 1 or 2. Examples of this amine compound include 2-hydroxyethylamine, 2,2'-dihydroxyethylamine, and 2-hydroxy-2-methyl-ethylamine.

In the method of the present invention, no limit is imposed on the amounts of the epoxy compound and the alkoxysilane compound added with respect to the ammonia, but in order to suppress the generation of by-products and obtain the silatrane derivative at a good yield, if the reaction is conducted under conditions where the ammonia is not lost by evaporation, then the epoxy compound should be used in an amount of 2 to 20 mol, and preferably 3 to 15 mol, per mole of ammonia. The alkoxysilane compound should be added in an amount of 0.5 to 50 mol per mole of ammonia, with a range of 1 to 20 mol being preferable. This means that it is recommended that the alkoxysilane compound be used in the approximate stoichiometric amount or in an excess amount with respect to the ammonia. In general, the generation of by-products will be suppressed if the alkoxysilane compound is used in an excess amount to the extent that the reaction does not slow down, but excess alkoxysilane compound will remain behind. This unreacted alkoxysilane compound that remains can be separated and recovered from the silatrane derivative by distillation or the like following the reaction. This reaction can also be conducted while ammonia gas is blown into a mixture of the epoxy compound and the alkoxysilane compound. When a reaction such as this is conducted in an open system, part of the ammonia will not react and will instead be released outside the system, so it must be used in an excess amount corresponding to this loss.

In the method of the present invention, no limit is imposed on the amounts of the epoxy compound and the alkoxysilane compound added with respect to the amine compound, but in order to obtain the silatrane derivative at a good yield, if y in the amine compound is 1, then the epoxy compound should be used in an amount of 0.5 to 10 mol, and preferably 0.8 to 5 mol, per mole of this amine compound, and if y in the amine compound is 2, then the epoxy compound should be used in an amount of 1.5 to 20 mol, and preferably 1.8 to 10 mol, with an amount of about 2 mol being particularly favorable. The amount in which the alkoxysilane compound is added should be 0.5 to 50 mol, and preferably 1 to 20 mol, per mole of the amine compound. This means that it is recommended that the alkoxysilane compound be used in the approximate stoichiometric amount or in an excess amount with respect to the amine compound. In general, the generation of by-products will be suppressed if the alkoxysilane compound is used in an excess amount to the extent that the reaction does not slow down, but excess alkoxysilane compound will remain behind. The unreacted alkoxysilane compound that remains can be separated and recovered from the silatrane derivative as needed by distillation or the like following the reaction.

With this method for preparing the silatrane derivative, the reaction will proceed either at room temperature or under heating, but heating to 100° C. or lower is preferred in order to reduce the reaction time. The use of an organic solvent is optional, but examples of organic solvents that can be used include hexane, heptane, octane, and other such aliphatic hydrocarbons; toluene, xylene, and other such aromatic hydrocarbons; methanol, ethanol, isopropanol, and other such alcohols; acetone, methyl isobutyl ketone, and other such ketones; diethyl ether, tetrahydrofuran, and other such ethers; ethyl acetate, isoamyl acetate, and other such esters; and dimethylformamide, dimethylacetamide, and other such amide compounds. The use of an alcohol such as methanol or ethanol in particular will allow the reaction time to be shortened and the targeted silatrane derivative to be obtained at an even better yield. When an alcohol is added, it is preferable to use an alcohol that has the same number of carbons as the silicon atom-bonded alkoxy groups in the raw material alkoxysilane compound so that the alkoxy groups bonded to silicon atoms will undergo an alkoxy group exchange reaction during the above reaction. Also, when an alcohol is added in the manufacturing method of the present invention, the reaction can be made markedly shorter, and the yield of the silatrane derivative that is obtained can be increased, by conducting the reaction at the reflux temperature of this alcohol.

The silatrane derivative of the present invention can be used, for example, to impart adhesive properties to silicone compositions cured by condensation reactions, silicone compositions cured by hydrosilylation reactions, silicone compositions cured by UV rays or other high-energy rays, and other such curable silicone compositions, as well as to alkoxysilane-modified polyether-based curable compositions, curable polyurethane resin and rubber compositions, curable epoxy resin compositions, curable polysulfide resin compositions, curable unsaturated polyester resin compositions, and other such curable compositions, or it can be used as a primer which increases the adhesion of the above-mentioned curable compositions when applied to the surface of a metal, glass, plastic, or other such substrate. The silatrane derivative is particularly useful with silicone compositions cured by condensation reactions, silicone compositions cured by hydrosilylation reactions, silicone compositions cured by UV rays or other high-energy rays, and other such curable silicone compositions.

The adhesion promoter of the present invention may be composed solely of the above-mentioned silatrane derivative, or of a mixture of this silatrane derivative with a known adhesion promoter or with a known organic solvent. When this silatrane derivative is used together with a known adhesion promoter, it loses its specific adhesion with respect to organic resins, but it displays good adhesion with respect to a variety of materials, such as organic resins, metals, and ceramics. Examples of known adhesion promoters that can be used together with this silatrane derivative include methyltrimethoxysilane, vinyltrimethoxysilane, allyltrimethoxysilane, 3-methacryloxypropyltrimethoxysilane, 3-glycidoxypropyltrimethoxysilane, 3-aminopropyltrimethoxysilane, N-(2-aminoethyl)-3-aminopropyltrimethoxysilane, bis(trimethoxysilyl)propane, and bis(trimethoxysilyl)hexane. The amino group-containing alkoxysilane or epoxy compound remaining unreacted through the process of manufacturing this silatrane derivative, as well as any reaction products other than the silatrane derivative produced by this reaction, may be left mixed in the final product. In this case, the silatrane derivative content should be at least 10 wt %, with at least 50 wt % being preferable and at least 70 wt % being even better. The reason for this is that the adhesion promotion effect will tend to be diminished if the silatrane derivative content is below this range.

The silatrane derivative of the present invention can also be included in a curable silicone composition. The curable silicone composition of the present invention is characterized by containing the above-mentioned silatrane derivative. Examples of curable silicone compositions containing this silatrane derivative include condensation reaction-curable silicone compositions cured by a condensation reaction such as a dealcoholization condensation reaction, a dehydration condensation reaction, a dehydrogenation condensation reaction, a de-oxime condensation reaction, a de-acetic acid condensation reaction, or a de-acetone condensation reaction; silicone compositions cured by hydrosilylation reactions; and high-energy ray-curable silicone compositions cured by high-energy rays, such as in a mercapto-vinyl addition reaction, an acrylic functional group radical reaction, or a cationic polymerization reaction for epoxy groups or vinyl ether groups. A silicone composition cured by a hydrosilylation reaction is particularly favorable.

No limit is imposed on the blend amount of the silatrane derivative in the curable silicone composition of the present invention, but the amount of the silatrane derivative should be from 0.01 to 20 wt %, and preferably from 0.05 to 10 wt %. A range of 0.1 to 5 wt % is particularly favorable.

The curable silicone composition of the present invention has a variety of uses, including molding. Since the curable composition of the instant invention contains a silatrane derivative, it displays specific adhesion with respect to organic resins. Thanks to this characteristic, the curable silicone composition can be utilized as a production material in casting molding. For example, in the case of an integrated molded article of cured silicone and an organic resin, the silicone adheres well to the organic resin but does not stick to the metal of the mold.

EXAMPLES

The silatrane derivative, adhesion promoter, and curable silicone composition of the present invention will now be described in further detail through practical examples.

Example 1

31.5 g (0.3 mol) of 2,2'-dihydroxyethylamine, 81.7 g (0.6 mol) of methyltrimethoxysilane, 45.7 g (0.4 mol) of allyl glycidyl ether, and 32 g of methanol were put into a 500 mL four-neck flask equipped with an agitator, a thermometer, and a reflux condenser. This system was heated and agitated for 5 hours at the methanol reflux temperature. Next, the entire amount of reaction mixture thus obtained was transferred to a pear-shaped flask, and the low-boiling component was distilled off by a rotary evaporator, which yielded 77.6 g of a faintly yellow transparent liquid. This transparent liquid was subjected to $^{29}$Si-nuclear magnetic resonance analysis and $^{13}$C-nuclear magnetic resonance analysis, which confirmed that the silatrane derivative expressed by the following formula had been produced:

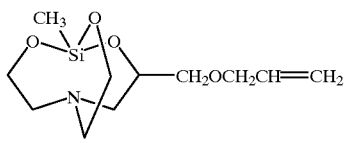

The content of this silatrane derivative was over 90 wt %. This transparent liquid was termed an adhesion promoter.

Example 2

12.2 g (0.2 mol) of 2-hydroxyethylamine, 81.7 g (0.6 mol) of methyltrimethoxysilane, 57.1 g (0.5 mol) of allyl glycidyl ether, and 32 g of methanol were put into a 500 mL four-neck flask equipped with an agitator, a thermometer, and a reflux condenser. This system was heated and agitated for 8 hours at the methanol reflux temperature. Next, the entire amount of reaction mixture thus obtained was transferred to a pear-shaped flask, and the low-boiling component was distilled off by a rotary evaporator, which yielded 63.3 g of a faintly yellow transparent liquid. This transparent liquid was subjected to $^{29}$Si-nuclear magnetic resonance analysis and $^{13}$C-nuclear magnetic resonance analysis, which confirmed that the silatrane derivative expressed by the following formula had been produced:

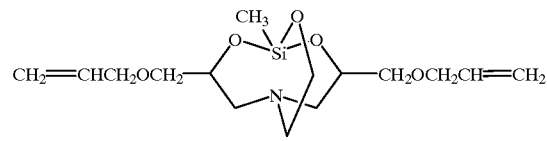

The content of this silatrane derivative was over 90 wt %. This transparent liquid was termed an adhesion promoter.

Example 3

31.5 g (0.3 mol) of 2,2-dihydroxyethylamine, 88.9 g (0.6 mol) of vinyltrimethoxysilane, 45.7 g (0.4 mol) of allyl glycidyl ether, and 32 g of methanol were put into a 500 mL four-neck flask equipped with an agitator, a thermometer, and a reflux condenser. This system was heated and agitated for 8 hours at the methanol reflux temperature. Next, the entire amount of reaction mixture thus obtained was transferred to a pear-shaped flask, and the low-boiling component was distilled off by a rotary evaporator, which yielded 63.5 g of a faintly yellow transparent liquid. This transparent liquid was subjected to $^{29}$Si-nuclear magnetic resonance analysis and $^{13}$C-nuclear magnetic resonance analysis, which confirmed that the silatrane derivative expressed by the following formula had been produced.

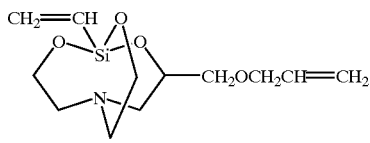

The content of this silatrane derivative was over 90 wt %. This transparent liquid was termed an adhesion promoter.

Comparative Example 1

12.2 g (0.2 mol) of 2-hydroxyethylamine, 81.7 g (0.6 mol) of methyltrimethoxysilane, 94.5 g (0.4 mol) of 3-glycidoxypropyltrimethoxysilane, and 32.0 g of methanol were put into a 500 mL four-neck flask equipped with an agitator, a thermometer, and a reflux condenser. This system was heated and agitated for 8 hours at the methanol reflux temperature. The entire amount of reaction mixture thus obtained was transferred to a pear-shaped flask, and the low-boiling component was distilled off by a rotary evaporator, which yielded 131.7 g of a faintly yellow transparent liquid. This transparent liquid was subjected to $^{29}$Si-nuclear magnetic resonance analysis and $^{13}$C-nuclear magnetic resonance analysis, which confirmed that the silatrane derivative expressed by the following formula had been produced.

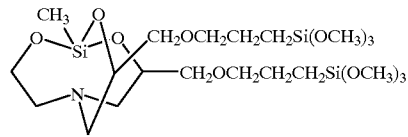

The content of this silatrane derivative was over 90 wt %. This transparent liquid was termed an adhesion promoter.

Examples 4 to 6 and Comparative Examples 2 and 3

A curable silicone composition was prepared as follows. A dimethylpolysiloxane sequestering agent terminated at both ends of the molecular chain with dimethylvinylsiloxy groups, fumed silica whose surface had been rendered hydrophobic by hexamethyldisilazane, a dimethylsiloxane/methylhydrodienesiloxane copolymer sequestering agent terminated at both ends of the molecular chain with trimethylmethoxy groups, phenylbutynol, and a platinum-based catalyst for use in a hydrosilylation reaction were uniformly mixed to prepare a hydrosilylation reaction-curable silicone composition.

The adhesion promoters prepared in Examples 1 to 3 and Comparative Example 1 were each blended in an amount of 1 wt % into this curable silicone composition to prepare four types of curable silicone composition. For the sake of comparison, a curable silicone composition not containing any of these adhesion promoters was separately readied. These curable silicone compositions were used to coat the surfaces of the substrates shown in Table 1, after which the coatings were cured by being heated for 30 minutes in a 120° C. circulating hot air oven. The cured products thus obtained were in a rubbery form. The adhesion of the five types of silicone rubber with respect to the substrates was evaluated, with a "○" indicating that the silicone rubber adhered well to a substrate, a "Δ" that the silicone rubber partially adhered to a substrate, and a "x" that the silicone rubber peeled completely away from the substrate. These evaluation results are given in Table 1.

TABLE 1

| | Present invention | | | Comparative examples | |
|---|---|---|---|---|---|
| | Ex. 4 | Ex. 5 | Ex. 6 | Comp. Ex. 2 | Comp. Ex. 3 |
| Type of adhesion promoter | Ex. 1 | Ex. 2 | Ex. 3 | Comp. Ex. 1 | none |
| Initial adhesion of silicone rubber | | | | | |
| Type of substrate | | | | | |
| Aluminum | x | x | x | ○ | x |
| Stainless steel | x | x | x | ○ | x |
| Glass | Δ | x | x | ○ | x |
| Polycarbonate resin | ○ | ○ | ○ | ○ | x |
| Polybutylene terephthalate resin | ○ | ○ | ○ | ○ | x |
| Phenol resin | ○ | ○ | ○ | ○ | x |

The silatrane derivative of the present invention is a novel compound and the method of preparing the silatrane derivative is efficient. The adhesion promoter of the present invention contains this novel silatrane derivative, and the curable silicone composition of the present invention containing the silatrane derivative displays specific adhesion with respect to organic resins.

That which is claimed is:

1. A silatrane derivative having the formula:

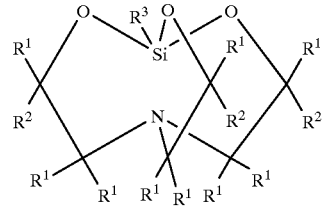

wherein each $R^1$ is independently a hydrogen atom or an alkyl group; each $R^2$ is independently selected from the group consisting of a hydrogen atom, an alkyl group, and an alkenyloxyalkyl group having the general formula:

$$-R^4-O-R^5$$

wherein $R^4$ is an alkylene group and $R^5$ is an alkenyl group, with the proviso that at least one $R^2$ is an alkenyloxyalkyl group; and each $R^3$ is independently selected from the group consisting of a monovalent hydrocarbon group, a $C_1$ to $C_{10}$ alkoxy group, a glycidoxyalkyl group, an oxiranylalkyl group, an acyloxyalkyl group, a haloalkyl group, and an aminoalkyl group.

2. The silatrane derivative according to claim 1, wherein $R^1$ is a hydrogen atom or a methyl group, $R^4$ is a methylene group, and $R^5$ is a C3 to C10 alkenyl group.

3. A method of preparing a silatrane derivative, said method comprising the step of reacting (i) an epoxy compound having the formula:

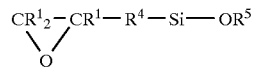

and (ii) an alkoxysilane compound having the formula:

$R^3Si(OR^6)_3$ with (iii) a compound selected from the group consisting of ammonia and an amine compound having the formula:

$NH_y(CR^1_2CR^1_2OH)_{(3-y)}$ wherein each $R^1$ is independently a hydrogen atom or an alkyl group; each $R^3$ is independently selected from the group consisting of a monovalent hydrocarbon group, a $C_1$ to $C_{10}$ alkoxy group, a glycidoxyalkyl group, an oxiranylalkyl group, an acyloxyalkyl group, a haloalkyl group, and an aminoalkyl group; $R^4$ is an alkylene group; $R^5$ is an alkenyl group; $R^6$ is a $C_1$ to $C_{10}$ alkyl group; and y is 1 or 2.

4. The method according to claim 3, wherein compound (iii) is ammonia and the epoxy compound is used in an amount from 3 to 15 moles per mole of the ammonia.

5. The method according to claim 3, wherein compound (iii) is an amine, y is 1, and the epoxy compound is used in an amount from 0.8 to 5 moles per mole of the amine compound.

6. The method according to claim 3, wherein compound (iii) is an amine, y is 2, and the epoxy compound is used in an amount from 1.8 to 10 moles per mole of the amine compound.

7. The method according to claim 3, wherein the alkoxysilane compound is used in at least about a stoichiometric amount relative to compound (iii).

8. The method according to claim 7, wherein compound (iii) is ammonia and the alkoxysilane compound is used in an amount from 1 to 20 moles per mole of the ammonia.

9. The method according to claim 7, wherein compound (iii) is an amine and the alkoxysilane compound is used in an amount from 1 to 20 moles per mole of the amine compound.

10. The method according to claim 7, wherein the alkoxysilane compound is used in a stoichiometric excess with respect to compound (iii), said method further comprising the step of separating the unreacted alkoxysilane compound from the silatrane derivative.

11. The method according to claim 3, wherein the reaction is carried out at a temperature not greater than 100° C.

12. The method according to claim 3, wherein the reaction is carried out in the presence of an alcohol having the same number of carbon atoms as $R^6$ in compound (ii).

13. An adhesion promoter comprising the silatrane derivative of claim 1.

14. The adhesion promoter according to claim 13, further comprising an alkoxysilane-containing adhesion promoter.

15. A curable silicone composition, comprising the silatrane derivative of claim 1.

16. The composition according to claim 15, wherein the curable silicone composition is curable by a hydrosilylation reaction.

17. The composition according to claim 15, wherein the silatrane derivative is present in an amount from 0.05 to 10 weight percent based on the total weight of the composition.

* * * * *